United States Patent [19]

Vinegar et al.

[11] Patent Number: 4,827,761

[45] Date of Patent: May 9, 1989

[54] SAMPLE HOLDER

[75] Inventors: Harold J. Vinegar; Scott L. Wellington, both of Houston, Tex.

[73] Assignee: Shell Oil Company, Houston, Tex.

[21] Appl. No.: 68,176

[22] Filed: Jun. 25, 1987

[51] Int. Cl.4 .............................................. H05G 1/00
[52] U.S. Cl. ........................................ 73/38; 378/208
[58] Field of Search ............................ 73/38; 378/208

[56] References Cited

U.S. PATENT DOCUMENTS

| | | | |
|---|---|---|---|
| 2,625,296 | 1/1953 | Parr . | |
| 2,737,804 | 3/1956 | Herzog et al. | 73/38 |
| 2,913,658 | 11/1959 | Burdine | 73/38 X |
| 4,304,122 | 12/1981 | Tentor | 73/38 |
| 4,599,891 | 7/1986 | Brauer et al. | 73/38 |
| 4,669,299 | 6/1987 | Closmann | 73/38 |
| 4,710,948 | 12/1987 | Withjack | 73/38 X |
| 4,769,602 | 9/1988 | Vinegar et al. | 324/303 |

Primary Examiner—Stewart J. Levy
Assistant Examiner—Joseph W. Roskos

[57] ABSTRACT

Sample holder apparatus for use in imaging (X-ray CT/NMR) apparatus is provided. The sample holder may be employed to conduct fluid flow studies on a sample and to measure petrophysical properties of a sample. The sample holder may consist of non-ferromagnetic, nonmetallic components; these components are: an outer tubular member containing end plugs that are restrained from outward movement by end member assemblies (which may be metallic) that releasably engage an engagement means, or raised shoulder, on the outer member, and an interior assembly, containing a sample, which is contained in the outer tubular member.

5 Claims, 3 Drawing Sheets

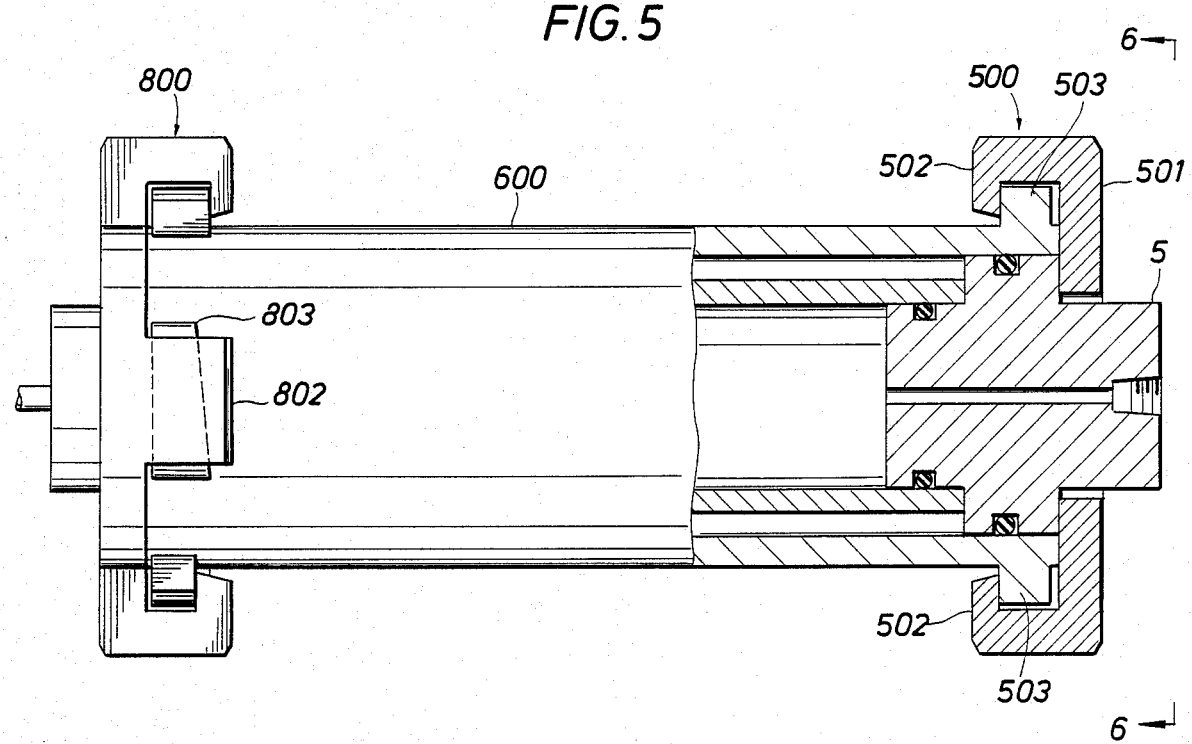
FIG. 5
FIG. 5A
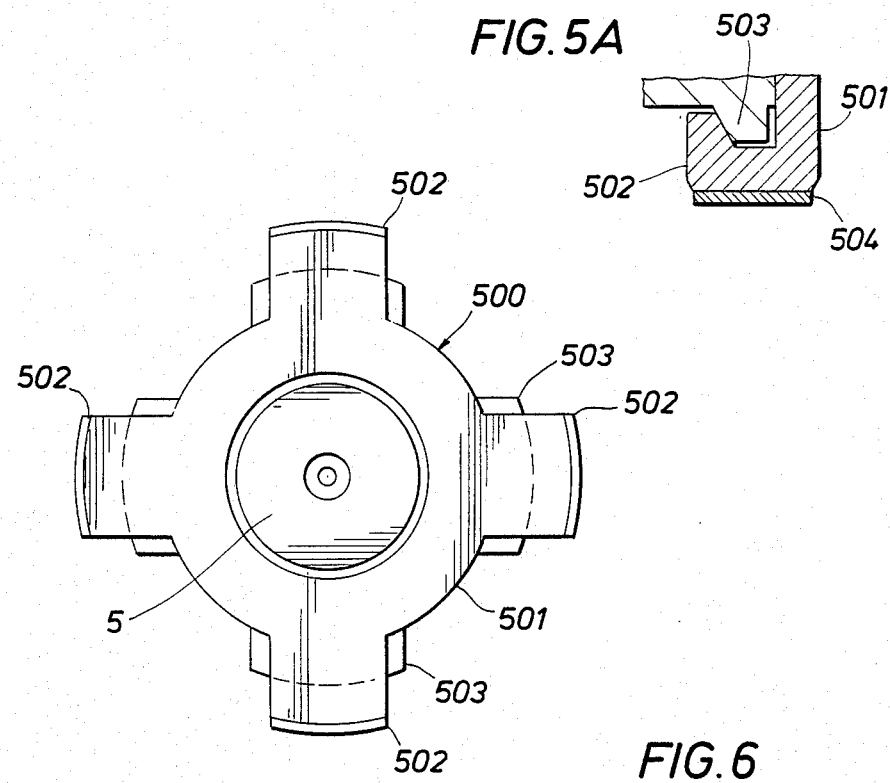
FIG. 6

SAMPLE HOLDER

BACKGROUND OF THE INVENTION

This invention relates to sample holders, and more particularly, relates to sample holders for use in imaging apparatus.

There are several methods available for nondestructively imaging a sample of material. For example., one such imaging technique is X-ray computerized tomography (CT) and another is nuclear magnetic resonance (NMR) imaging. For X-ray CT imaging it is desirable that any sample holder have a minimum attenuation or absorption of X-rays in the energy range employed to scan a sample. In a similar fashion, the sample holder for use in NMR imaging should employ materials which are nonferromagnetic and nonmetallic to avoid influencing the magnetic and electromagnetic fields of the NMR imaging apparatus. In particular, it is desirable to have a sample holder which may be employed sequentially in both an NMR imaging apparatus and an X-ray CT scanner without removing the sample from the sample holder.

Additionally, if it is desired to measure petrophysical properties of a sample by using NMR or CT scanner apparatus, it is necessary that the sample holder be able to subject the sample to extreme temperatures and pressures. Further, the sample holder should be able to introduce fluids into the sample and remove fluids from the sample, while subjecting the sample to these pressures and/or temperatures.

There exists, therefore, an unfulfilled need for a sample holder that allows for subjecting a sample to extreme temperatures and/or pressures while conducting fluids through such a sample, that may be employed in imaging apparatus.

These and other limitations and disadvantages of the prior art are overcome by the present invention, however, and an apparatus for containing a sample while allowing for measurement of petrophysical properties of such a sample and for conducting fluid flow studies through such a sample is provided.

SUMMARY OF THE INVENTION

In a preferred embodiment of the present invention, a sample holder is provided which may be employed in an imaging apparatus, such as for example, but not limited to, either X-ray CT scanning apparatus or NMR imaging apparatus, or both, to allow for measurement of petrophysical characteristics of a sample by such an imaging apparatus and to allow for fluid flow studies to be conducted on a sample while in such an imaging apparatus.

More specifically, the preferred embodiment of the present invention has nonmetallic, non-ferromagnetic components that include a tubular member having engagement means which are preferably outer flange-like raised shoulders, near its two extreme ends and removable end member assemblies, a portion of which abuts against and engages these engagement means or shoulders. End plugs are disposed sealingly in the ends of the tubular member and are disposed against a portion of said end member assemblies. A non-metallic, non-ferromagnetic, interior assembly is also contained inside said tubular member. This interior assembly is preferably centrally located, but may be disposed adjacent one of said end plugs; the interior assembly preferably includes a hollow inner member disposed on two movable plug members to define an interior volume for containing a sample.

It is an object of the present invention to provide a sample holder for use in either NMR imaging apparatus, or X-ray CT scanning apparatus, or both, that may be employed to determine petrophysical properties of a sample and to conduct fluid flow studies on a sample.

These and other features and objects of the present invention will become apparent from the following detailed description, wherein reference is made to the Figures in the accompanying drawings.

IN THE DRAWINGS

FIG. 5 is a partially cross-sectional, pictorial illustration of an alternative embodiment of the present invention.

FIG. 5A is a pictorial illustration, in cross-section, of a modification to a portion of the apparatus depicted in FIG. 5.

FIG. 6 is an end-view of the embodiment depicted in FIG. 5.

DETAILED DESCRIPTION

Figure 1:
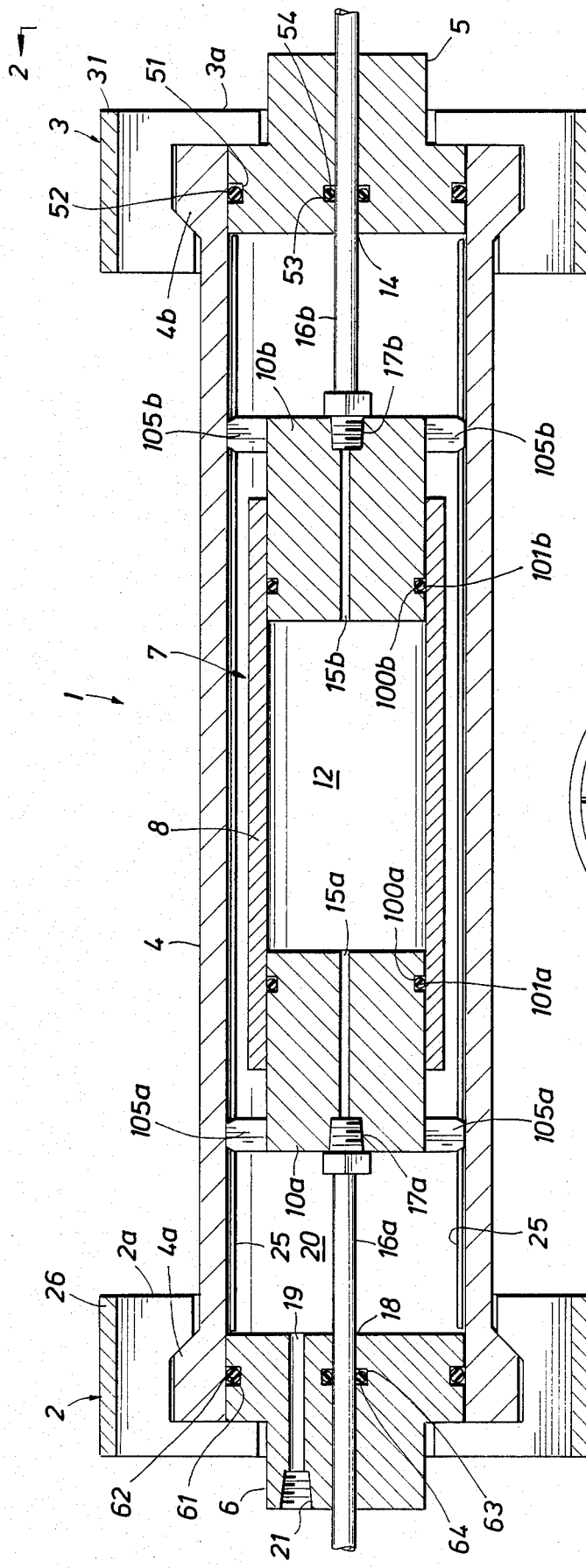
FIG. 1 is a cross-sectional, pictorial illustration of one embodiment of the present invention.

Referring now to FIG. 1, there may be seen a simplified cross-sectional, pictorial illustration of the presently preferred embodiment of the present invention. More specifically, there may be seen a cross-section of sample holder 1 of the present invention. Sample holder 1 is seen to consist of end member assemblies 2 and 3 mounted or disposed around a tubular or cylindrical outer member 4. Member 4 has engagement means 4a, 4b which may be a continuous raised or flange-like shoulder near each extreme end. This shoulder may have an inclined portion that contacts and restrainedly and releasably engages corresponding portions or faces in end member assemblies 2, 3.

Continuing to refer to FIG. 1, there may also be seen end-plugs 5, 6 which are sealingly interfaced with the interior bore of outer member 4 and thus provide, in combination with member 4, a fluid-tight outer pressure retaining assembly, as discussed further later herein. There may also be seen an interior assembly 7. Assembly 7 consists of a pressure retaining and transmitting member 8 which may be sealingly attached to moveable plug members 10a, 10b. Pressure member 8, and moveable plugs 10 define a volume or chamber 12 for containing a sample (not shown) of an appropriate size. Where comparable elements have the same name and item number, except one is "a" and the other is "b" (i.e. 10a and 10b for moveable plugs), the use herein of the item number without the "a" or "b" (i.e. only 10) means either or both of the elements that have the same numeric item number. Pressure member 8 may be for example, but not limited to, a shrink-fit teflon sleeve that is appropriately shrunk onto a sample and plugs 10.

End-plug 5 contains therethrough an opening 14 sealingly containing conduit means 16b; this conduit means 16b may be employed to introduce fluid(s), via opening 15b in plug 10b, into a sample (not shown) contained in chamber 12. The fluid introduced into the sample located in chamber 12 may then be removed by opening 15a which passes through moveable plug 10a. In turn the fluid passing through opening 15a may be removed by conduit means 16a which is suitably secured to moveable plug 10a by means of threads or other securing means 17a; conduit means 16b is similarly secured to plub 10b by securing means 17b. Conduit means 16a sealingly passes through an appropriate opening 18 throuh end-plug 6. End-plug 6 also contains therethrough an opening 19 for injecting fluid into opening 20 and to allow for applying fluid pressure to member 8 and movable plugs 10 by a pressurized fluid via opening 19, to thereby apply pressure on a sample located in chamber 12. Also, opening 19 in end-plug 6 has threaded or securing means 21 for appropriate connection of conduit means (not shown) for supplying such a fluid whether pressurized or not, into the interior chamber or opening 20. In addition, other pressure resistant openings (not shown), in either, or both end plug for sealingly containing appropriate pressure and/or for temperature probes, heating means, etc., may be provided.

Member 8 may be used to ensure that fluid flows through the sample rather than around the sample; this is normally desired, for example for fluid flow studies. Further, member 8 may provide for applying pressure to a sample, as noted hereinabove. Preferably, member 8 is an elastomer sleeve disposed in a fluid-tight manner around a sample. Such elastomers may be, by way of example, rubber (for high temperatures, a rubber such as Viton), silicone rubber (for higher temperatures), shrink-fit teflon, Kalrez (a DuPont high temperature elastomer), or appropriate combinations thereof, i.e. rubber over a shrink-fit teflon sleeve, where the teflon sleeve is sized to seal the outside surface of the sample to prevent fluid flow around the sample and the rubber sleeve provides a seal with each movable plug 10 and the teflon sleeve.

Moveable plugs 10 may be constructed of high temperature Vespel (DuPont) or Torlon (Amoco Chemicals Co.) polymers. Similarly, conduits 16 may be constructed of teflon, Vespel, or Torlon.

Figure 2:
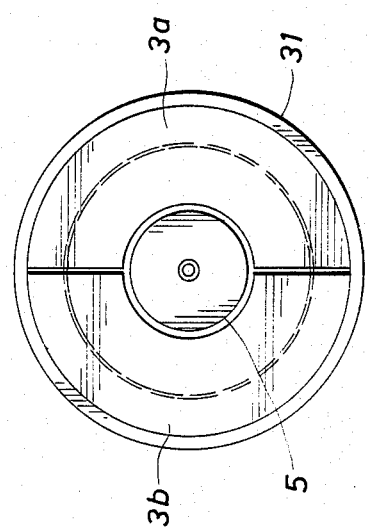
FIG. 2 is a pictorial illustration of an end-view of the apparatus illustrated in FIG. 1.

Referring now to FIG. 2, there may be seen an end-view of end member assembly 3. It may be seen from FIG. 2 that end member assembly 3 may consist of two mating cylindrical or C-shaped halves, 3a, 3b that have appropriate openings, indentations or recesses therein for member 4 and its raised shoulder portion 4b, and have an appropriately sized opening to allow for access to end plug 5 while still allowing for restraint of end plug 5 from any outward movement. These two halves 3a, 3b are suitably placed around member 4 and its raised shoulder 4b. as well as end plug 5, then mated and held together by removeable connection means 31, such as a band member as shown, which may be retained in place by an appropriate set screw (not shown) in member 31. Halves 3a, 3b may be partially interlocking with each other at their mating surfaces. Band 31 is preferably a one-piece high-strength member that removably mounts around the mated halves of the end member assembly to maintain the halves in their mated configuration.

Although depicted as two mating halves, 3a, 3b the portions of end member 3 that engage the engagement means 4b on member 4 may be any number of mating portions, such as, for example, but not limited to thirds or quarters, to more fully equalize any stresses on band member 31. Also seen in FIG. 2 is a partial view of the end of end-plug 5, opening 14 and conduit 16b therein (items 14 and 16b are not so identified on FIG. 2). End member assembly 2 is similarly constructed and employs removable band member 26.

As seen from FIGS. 1 and 2, end member assembly 3 is disposed adjacent outer member 4 and engages the engagement means 4b shown as a continuous raised shoulder near the one end of member 4, but in a releasable manner since end member assembly 3 has two cylindrical halves (3a, 3b) that are connected together by removable connection means 31, for example, the band member shown. Similarly, it may also be seen that end plug 5 is restrained from movement out of member 4 by a portion of end member assembly 3, which is in turn restrained from lateral movement by the shoulder 4b on member 4. It may also be seen that end member 3 assembly has an opening therein for a portion of end plug 5 to project therethrough to allow for conduit means 16b and any other appropriate connections made through plug 5 to have access to plug 5, and an extended lip or projection for engaging and restraining the body of end plug 5 from any outward motion, as noted hereinbefore. End plug 6 and end member assembly 2 are similarly constructed and operate in a similar fashion. Although end plugs 5, 6 are shown with outwardly projecting portions, these portions may project inward, and the opening in end member assemblies 3, 4 need only be large enough to enable appropriate connections to and through end plugs 5, 6.

Referring again to FIG. 1 it may be seen that end member assemblies 2 and 3 (via halves 2a, 2b, and 3a, 3b) contact and are releasably restrained by or engage an appropriate engagement means (4a, 4b), such as the flange-like or raised shoulder shown, near the extreme ends of outer member 4. In this manner, any pressure in chamber 12 and/or 20 forces end-plugs 5 and 6 into releasably restrained engagement with a portion of end member assemblies 2 and 3, which are correspondingly restrained from any lateral motion by releasably restrained engagement with appropriate engagement means (4a, 4b) such as the flange-like shoulders, near the extreme ends of member 4, and any radially outward movement, i.e. movement of unmating or separation, by the end member portions is prevented by suitable removeable connection means, such as bands 31, 26. In this manner member 4, end-plugs 5 and 6, and end member assemblies 2 and 3 form an outer pressure retaining assembly or boundary.

End-plug 5 may have therein a pressure resistant sealing means, such an appropriate groove or slot 51 for containing an O-ring 52, to provide a pressure resistant sealing or fluid-tight interface between the interior surface of member 4 and the exterior surface of end-plug 5. Although only one such slot 51 is shown in FIG. 1 more than one such slot may be so employed for this and any other pressure resistant sealing means noted herein. End-plug 5 may also contain such a sealing means, such as groove 53 suitable for containing O-ring 54, for providing such a sealing interface with conduit means 16b, even if conduit means 16b may be movable. In a similar manner end-plug 6 may have a pressure resistant sealing means, such as machined slot 61 for containing an O-ring 62, to provide a sealing interface between end-plug 6 and the interior surface of member 4. Further, end-plug 6 may contain a sealing means, such as machined groove 63, suitable for containing O-ring 64, as a pressure retaining means for providing a sealing interface with conduit 16a, which may be moveable. In a similar fashion, either or both movable plug 10 may have thereon a sealing means, such as slot 100 (100a, 100b) for containing O-ring 101 (101a, 101b)-, for maintaining a pressure resistant, slidable, sealing interface with member 8.

Moveable plugs 10a, 10b also have spacers 105a, 105b that center plugs 10a, 10b and any sample therebetween in the center of the interior opening 20 of member 4. Although one set of such spacers 105 is shown, more than one set may be so employed, and spacers 105 may be sized to fit over member 8 as well as plugs 10, so that spacers may be placed anywhere along the plugs 10, or member 8. In this manner the sample may be positioned in the middle of the magnetic fields of an NMR imaging apparatus. Plugs 10a, 10b, member 8 and conduit means 16a, 16b are made of appropriate materials depending upon the imaging apparatus employed, as noted hereinbefore and hereinafter.

A sample may be positioned in chamber 12 such that its end faces abut respectively the interior face of movable plug 10a and the interior face of moveable plug 10b, or an appropriate permeable membrane may be disposed between the sample and the movable plug. In this manner fluids may be introduced into the sample via conduits 16 and openings 15, in either direction, as desired, with at least a portion of member 8 preventing fluid flow around, rather than through, the sample. In a similar manner fluid may be introduced via opening 19 in end-plug 6 to provide pressure in interior chamber 20 thereby subjecting the sample to external pressure through member 8 and moveable plugs 10. Thus, it may be seen that a sample may be positioned in the sample holder of the present invention and subjected to pressure while easily conducting various fluids into or out of the sample.

Appropriate heating means 25 may also be included to provide the necessary temperature range appropriate for a particular sample by convective heating and heat flow inside member 4, since member 4 is normally a good thermal insulator. More specifically, non-magnetic and non-metallic heater elements 25 may be included within opening 20 to heat the fluid therein, or alternatively, the fluids may be externally heated by a separate heater means and injected into opening 20, or then passed through appropriate non-metallic tubing wrapped around the outside of member 4 (not shown), or injected through the sample. Another alternative is to heat the sample indirectly by heating member 4 by means of external infra-red radiation directed at member 4.

Preferably, at least one carbon resistor, as a heater means 25, is disposed within opening 20 and may extend the maximum length possible down the interior wall of member 4, to minimize the need for convection heating down the length of the interior of member 4. Suitable additional openings (not shown) may be provided in either or both of end plugs 5, 6 to power such resistor(s). Any such resistor(s) may be appropriately sized to provide the desired heatup rate; optionally, several resistors may be employed for heatup and one or more resistor(s) employed to maintain a fixed temperature.

Figure 3:
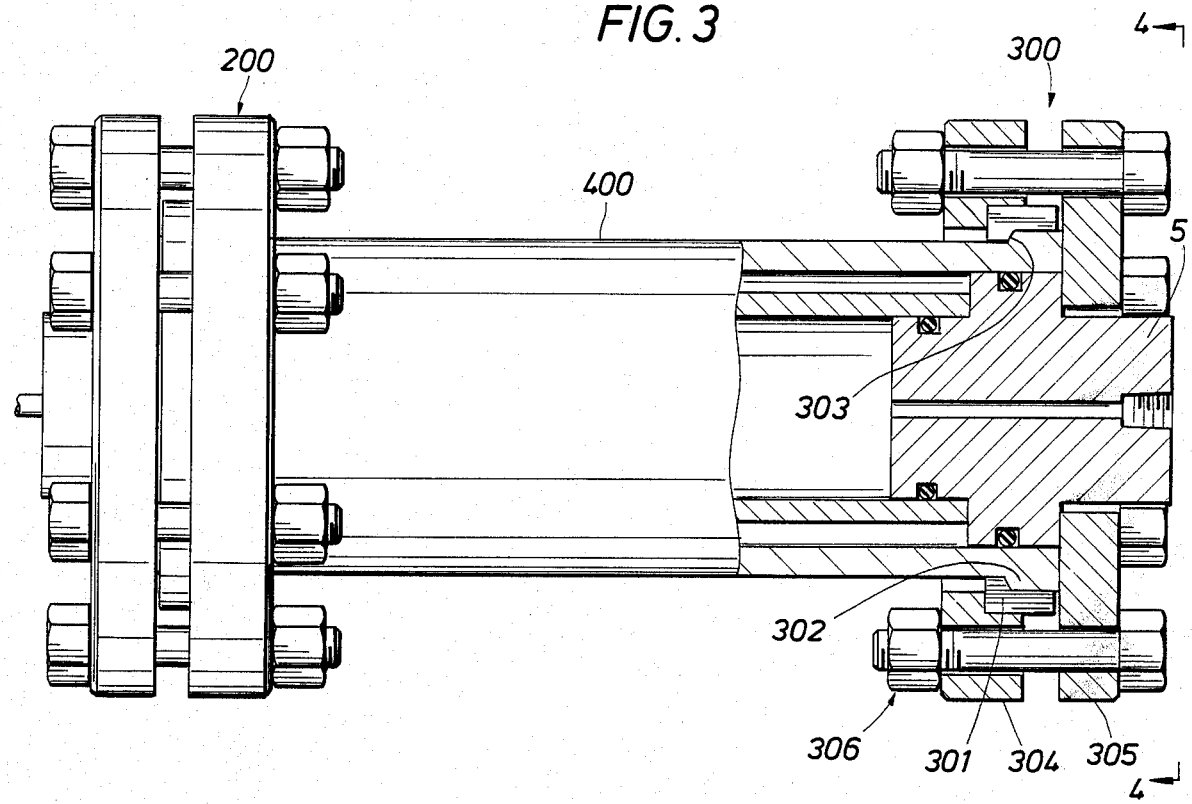
FIG. 3 is a partially cross-sectional, pictorial illustration of an alternative embodiment of the present invention.
Figure 4:
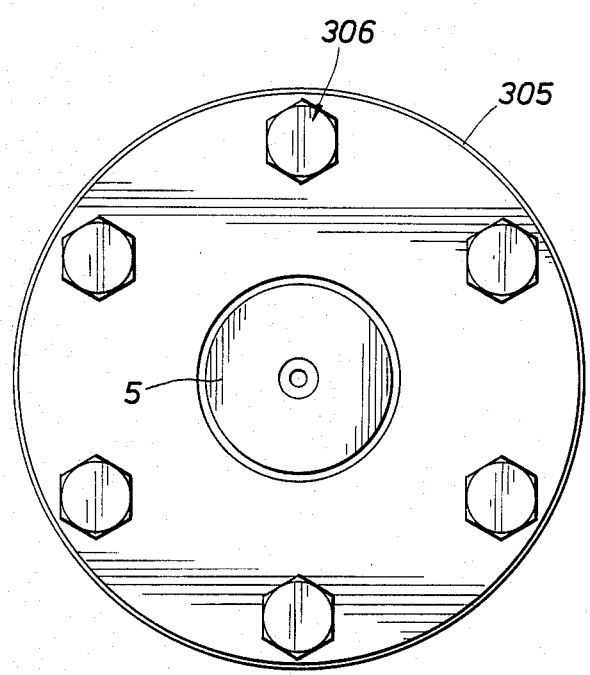
FIG. 4 is an end-view of the embodiment depicted in FIG. 3.

Referring now to FIGS. 3 and 4, there may be seen an alternate embodiment of the present invention. More particularly, FIG. 3 depicts a different arrangement of the end member assemblies from that shown in FIGS. 1 and 2. In FIG. 3, end member assembly 300 is seen to consist of a removable split ring 301 releasably restrained by a continuous raised shoulder 302 near the end of outer member 400 and having thereon an inclined face 303. Split ring 301 is preferably made of two mating halves, similar to halves 3a, 3b, as shown in FIG. 2. End member assembly 200 is constructed similarly to end member assembly 300.

Split ring 301 is held against shoulder 302 by removable inner ring 304 that is interconnected with outer ring 305 by appropriate connection means 306, such as the bolts and nuts shown in FIG. 3, that are removable. Although the engagement means 302 are depicted as a raised shoulder, it is also possible for the engagement means to be a tapered slot or groove (not shown) in outer member 400 into which the split ring 301 may fit and engage the walls or shoulder of this slot or groove. The inside diameter of ring 304 is greater than the maximum outside diameter of shoulder 302 or member 400, to allow for ring 304 to be removed from outer member 400, while being of smaller inside diameter than the outside diameter of split ring 301. Outer ring 305 holds end plug 5 in place in a manner similar to that described for the FIGS. 1 and 2 embodiment of the present invention. FIG. 4 is an end view of outer ring 305 showing the ends of the connection means 306 and a partial end view of end plug 5. The remainder of the apparatus is as described hereinbefore.

Referring now to FIGS. 5 and 6, there may be seen yet another alternate embodiment of the present invention. Again, FIG. 5 depicts a different arrangement for the end member assemblies from that of FIG. 1. In FIG. 5, end member assembly 500 is seen to consist of an outer ring 501 that has separate, spaced apart, projecting fingers 502 that interlock with corresponding separate spaced-apart raised shoulders 503 near the ends of outer member 600. End member assembly 800 is similarly constructed and arranged. In FIG. 6, an end view of end member assembly 500 is shown and assembly 500 has, for illustrative purposes only, four separate fingers 502; any appropriate number of fingers 502 and shoulders 503 may be employed for end member assemblies 500, 800. Thus, fingers 502 are initially inserted between shoulders 503 and then end member assembly 500 is rotated to interlock the fingers with the shoulders. As also depicted in shadow in FIG. 5, for end member assembly 800, the interlocking faces of fingers 802 and shoulders 803 may be inclined to provide a more positive engagement. FIG. 6 depicts an end view of end member assembly 500 and a portion of end plug 5.

Referring now to FIG. 5A, there may be seen, in cross-section, a modification to a portion of the apparatus depicted in FIG. 5. In particular, shoulders 503 and fingers 502 are seen to have inclined faces, similar to those depicted in FIG. 1. These inclined faces on shoulders 503 may be employed to reduce stresses generated in shoulders 503 and member 600. For this arrangement, it is preferred to add a removable band member 504 around the fingers 502 to prevent the fingers from slipping up the inclined face of shoulders 503 under load. Band member 504 is preferably a one-piece member that removably slips over fingers 502 after the fingers are engaged with shoulders 503.

In a manner similar to that described hereinbefore, end member assemblies 500, 800 restrain end plugs 5, 6 from outward motion to provide in conjunction with outer member 600 an outer pressure retaining assembly. The remainder of the apparatus may be as described hereinbefore.

Although depicted and described herein as employing two similar types of end member assemblies in the present invention, the present invention also includes the use of one type of end member assembly at one end of the outer tubular member and any other type of end member assembly at the other end of the outer tubular member.

Thus, in summary it may be seen that the apparatus of the present invention has an outer tubular member having engagement means thereon, containing end plugs in the ends of the tubular member that are restrained from outward movement by end member assemblies, which are in releasable engagement with the engagement means, and containing therein an interior assembly.

Preferably, any outer member (4; 400; 600), end plugs (5, 6) and interior assembly (7) are constructed of non-metallic, non-ferro-magnetic materials; any end member assemblies (2, 3; 200, 300; 500, 800) may be constructed of metals or metallic materials, if desired. This construction allows for all of the sample holder, except the end members, to be located inside the bore of the magnets for NMR apparatus; similarly, for X-ray CT apparatus the end member assemblies are spaced along the outer member (4; 400; 600) away from the sample chamber 12 and
do not influence the X-rays passing through chamber 12 containing a sample. For NMR, the end members are preferably non-ferromagnetic, such as nonmagnetic stainless steel or Monel K500.

For X-ray CT, the entire sample holder may be made from any metal that has low X-ray absorption and/or attenuation properties. For NMR, the sample holder (less end members) may be made from nonmetallic and non-ferromagetic materials. For both NMR and X-ray, the NMR material selection is most restrictive and accordingly nonmetallic, non-ferromagnetic materials should be employed; such nonmetallic, nonferromagnetic materials normally have acceptably low X-ray attenuation characteristics.

For such dual uses, appropriate materials may be pressure and temperature resistant plastics, epoxies, polyester resins, polymers, or polymer composites (laminates). The polymer can be reinforced with glass, kevlar, graphite, or ceramic fibers. One such composite polymer is a homopolymerized oxirane oligimer, such as Pyroite TM, a polymer from Pyroite Polymers International, Inc. in Avon, Ohio. Spatially oriented type S-glass or E-glass fibers are embedded in the oligimer. The fibers are circumferential hoops or axial members; the axial members are wrapped in a helix with a large helix angle (measured relative to a line parallel to the axial centerline). Type S-glass is preferred for X-ray CT since it contains no calcium oxide with high X-ray attenuation, as does the E-glass. Graphite is not recommended for NMR usage because of its radiofrequency attenuation due to its conductivity.

Those portions of the apparatus that make up the outer pressure retaining assembly should be designed and fabricated in accordance with the ASME Boiler and Pressure Vessel Code Section X (Fiberglass Reinforced Plastic Pressure Vessels); some design calculations (end member assemblies, engagement means, and end plugs) may be made as disclosed in Section VIII, Division 1, but using the restrictions of Section X.

Particular attention should be paid to the fact that any metallic and nonmetallic members may have appreciable differences in thermal expansions; this may lead to high stresses at the ends of the outer member 4 and its shoulders or flange-like projections.

Many other variations and modifications may be made in the apparatus and techniques hereinbefore described, by those having experience in this technology, without departing from the concepts of the present invention. Accordingly, it should be clearly understood that the apparatus depicted in the accompanying drawings and referred to in the foregoing description is illustrative only and is not intended as any limitation on the scope of the invention.

What is claimed:

1. A sample holder comprising:
   (a) tubular member having a continuous raised shoulder disposed around the exterior of said tubular member near the extreme ends of said tubular member as an engagement means,
   (b) first and second end plugs disposed sealingly in the ends of said tubular member,
   (c) end member assemblies disposed adjacent said tubular member in a manner to releasably engage said engagement means and in a manner to restrain said end plugs in said tubular member, and wherein at least one of said end member assemblies comprises mating cylindrically-shaped members having indentations therein for said tubular member and said continuous raised shoulder and an opening therein for access to said end plugs, and a continuous band removably disposed around the exterior of said cylindrical members for releasably maintaining said cylindrical members in a mated position,
   (d) interior assembly disposed within said tubular member for containing a sample and wherein said interior assembly comprises, a first and second moveable plug, and an inner tubular member having an opening therethrough for containing a sample and disposed sealingly around said moveable plugs,
   (e) means for applying pressure to said inner tubular member, and
   (f) means for conducting fluids into and out of said opening of said inner tubular member.

2. A sampler holder comprising:
   (a) tubular member having a continuous raised shoulder disposed around the exterior of said tubular member near the extreme ends of said tubular member as an engagement means,
   (b) first and second end plugs disposed sealingly in the ends of said tubular member,
   (c) end member assemblies disposed adjacent said tubular member in a manner to releasably engage said engagement means and in a manner to restrain said end plugs in said tubular member, and wherein at least one of said end member assemblies each comprise,
   inner ring member disposed around said tubular member,
   outer ring member disposed adjacent an end of said tubular member and releasably interconnectable with said inner ring member, and
   split ring members disposed between said inner and outer ring member and adjacent and restrained by said shoulder and said inner ring member,
   (d) interior assembly disposed within said tubular member for containing a sample, and wherein said interior assembly comprises, a first and second moveable plug, and an inner tubular member having an opening therethrough for containing a sample and disposed sealingly around said moveable plugs, (e) means for applying pressure to said inner tubular member, and (f) means for conducting fluids into and out of said opening of said inner tubular member.

3. A sample holder comprising:

(a) tubular member having thereon a first plurality of spaced apart, raised shoulders in a circular configuration around the exterior of said tubular member near the extreme ends of said tubular member as an engagement means, (b) first and second end plugs disposed sealingly in the ends of said tubular member, (c) end member assemblies disposed adjacent said tubular member in a manner to releasably engage said engagement means and in a manner to restrain said end plugs in said tubular member, (d) interior assembly disposed within said tubular member for containing a sample, and wherein said interior assembly comprises, a first and second moveable plug, and an inner tubular member having an opening therethrough for containing a sample and disposed sealingly around said moveable plugs, (e) means for applying pressure to said inner tubular member, and (f) means for conducting fluids into and out of said opening of said inner tubular member.

4. The sample holder of claim 3, wherein said end member assemblies each comprise a ring member having a first plurality of fingers extending therefrom for rotatably and releasably interlocking with said plurality of shoulders.

5. The sample holder of claim 4, further comprising, a continuous band member removably disposed around said fingers.

* * * * *